United States Patent [19]
Yin et al.

[11] Patent Number: 5,454,164
[45] Date of Patent: Oct. 3, 1995

[54] WET SHAVING SYSTEM WITH A LUBRICATING DEVICE

[75] Inventors: Yuling Yin, Quincy; Mingchih M. Tseng, Hingham, both of Mass.

[73] Assignee: The Gillette Company, Boston, Mass.

[21] Appl. No.: 210,182

[22] Filed: Mar. 17, 1994

[51] Int. Cl.⁶ ................................. B26B 19/44
[52] U.S. Cl. ................................. 30/41; 30/50
[58] Field of Search ................. 30/41, 47–50; 83/14; 428/425.8; 424/73

[56] References Cited

U.S. PATENT DOCUMENTS

| | | | |
|---|---|---|---|
| 4,170,821 | 10/1979 | Booth | 30/41 |
| 4,778,640 | 10/1988 | Braun et al. | 264/250 |
| 5,095,619 | 3/1992 | Davis et al. | 30/41 |
| 5,113,585 | 5/1992 | Rogers et al. | 30/41 |

FOREIGN PATENT DOCUMENTS

| | | | |
|---|---|---|---|
| 2024082 | 1/1980 | United Kingdom | 30/41 |
| WO93/16135 | 8/1993 | WIPO | 30/41 |

*Primary Examiner*—Douglas D. Watts
*Attorney, Agent, or Firm*—Stephan P. Williams

[57] ABSTRACT

The present invention is directed to a shaving system of the wet shave type comprising a blade member (one or more) and a structure which supports or holds the blade member and which has an external skin engaging portion in proximity to the blade member.

The skin engaging portion includes an improved shaving aid composite which comprises a matrix of a water-insoluble polymer, an effective amount of a skin lubricating water-soluble polymer dispersed within the matrix, and a compatibilizer material that improves the compatibility of the water-soluble polymer with the water-insoluble polymer so as to reduce the domain size of the water-soluble polymer within the matrix. The improved shaving aid composite provides a greater and more sustained release of the water-soluble polymer during use while maintaining good mechanical integrity. The preferred shaving composite comprises about 15 to 40% polystyrene, about 40 to 80% polyethylene oxide, and about 0.5 to 15% compatibilizer material such as polyethylene oxide—polypropylene oxide copolymer.

17 Claims, 1 Drawing Sheet

WET SHAVING SYSTEM WITH A LUBRICATING DEVICE

BACKGROUND OF THE INVENTION

The present invention relates to a shaving system of the wet shave type, more particularly to a shaving system with an improved shaving aid composite.

It is now well known that shaving comfort can be enhanced by affixing to a razor cartridge a shaving aid composite, also known as a lubricating strip, which continuously releases a shaving aid, typically a lubricant, during the shaving process. See, for example, U.S. Pat. No. 4,170,821 and GB 2,024,082. The shaving aid composite generally comprises a water insoluble polymer matrix, typically polystyrene, and a water soluble shaving aid, typically polyethylene oxide, which leaches out of the composite during shaving to enhance shave comfort. The addition of a small amount of plasticizer such as propylene glycol to improve the processing of injection molded shaving aid composites is disclosed in U.S. Pat. No. 4,778,640.

Unfortunately, conventional shaving aid composites suffer from the disadvantage that they release an insufficient amount of the shaving aid, particularly after the first three or four shaves where release of the shaving aid may drop off to negligible quantities. Accordingly, recent efforts have been made to improve shaving aid composites so as to enhance and prolong release of the shaving aid. Such efforts have resulted in improved shaving aid composites which include the following: incorporation of low molecular weight release enhancing agent, such as polyethylene glycol, into the matrix, disclosed in U.S. Pat. No. 5,113,585; the use of ethylene vinyl acetate copolymer as the matrix material, disclosed in U.S. Pat. No. 5,349,750; and incorporation of a water-swellable polymer such as Salsorb 84, a cross-linked polyacrylic, disclosed in U.S. Ser. No. 08/121,153. All of the aforementioned patents or patent applications are incorporated herein by reference.

SUMMARY OF THE INVENTION

The present invention is directed to a shaving system of the wet shave type comprising a blade member (one or more) and a structure which supports or holds the blade member and which has an external skin engaging portion in proximity to the blade member. The shaving system may be a disposable shaving cartridge adapted for coupling to and uncoupling from a razor handle or it may be a shaving head which is integral with a razor handle so that the complete razor is discarded as a unit when the blade or blades become dulled. The blade edge cooperates with the skin engaging portion to define shaving geometry.

The skin engaging portion includes an improved shaving aid composite which comprises a matrix of a water-insoluble polymer, an effective amount of a skin lubricating water-soluble polymer dispersed within the matrix, and a compatibilizer material that improves the compatibility of the water-soluble polymer with the water-insoluble polymer so as to reduce the domain size of the water-soluble polymer within the matrix. The improved shaving aid composite provides a greater and more sustained release of the water-soluble polymer during use while maintaining good mechanical and structural integrity.

DESCRIPTION OF THE PREFERRED EMBODIMENTS

Figure 1:
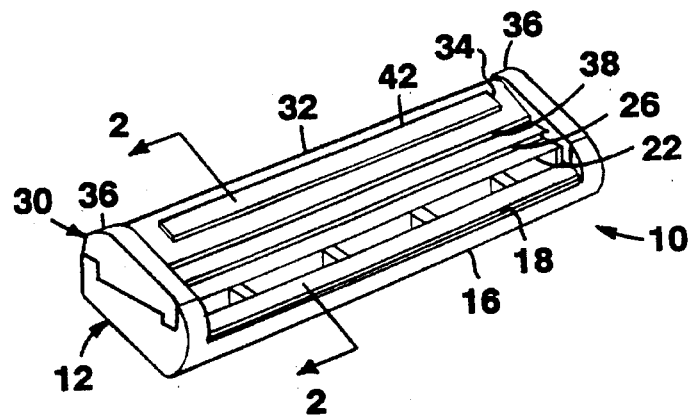
FIG. 1 is a perspective view of a razor unit in accordance with the invention.
Figure 2:
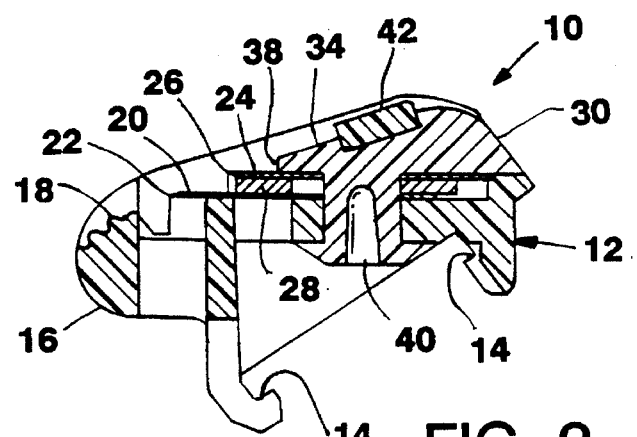
FIG. 2 is a sectional view taken along the line 2—2 of FIG. 1.

The shaving unit 10 shown in FIGS. 1 and 2 includes base or platform member 12 molded of high impact polystyrene that includes integral coupling groove structure 14 for attachment to a razor handle and guard structure 16 that defines a transversely extending forward skin engaging surface 18. On the upper surface of platform 12 are disposed steel leading blade 20 having a sharpened edge 22, steel following blade 24 having sharpened edge 26, and aluminum spacer member 28 that maintains blades 20 and 24 in spaced relation. Cap member 30 is molded of high impact polystyrene and has body portion 32 that defines skin engaging surface 34 that extends transversely between forwardly projecting end walls 36 and has a front edge 38 that is disposed rearwardly of blade edge 26. Integral rivet portions 40 extend downwardly from transversely extending body portion 32 and pass through holes in blades 20 and 24, spacer 28, and platform 12 to secure cap 30, blades 20, 24 and spacer 28 on platform 12. Adhesively affixed to skin engaging surface 34 is shaving aid composite 42.

Figure 3:
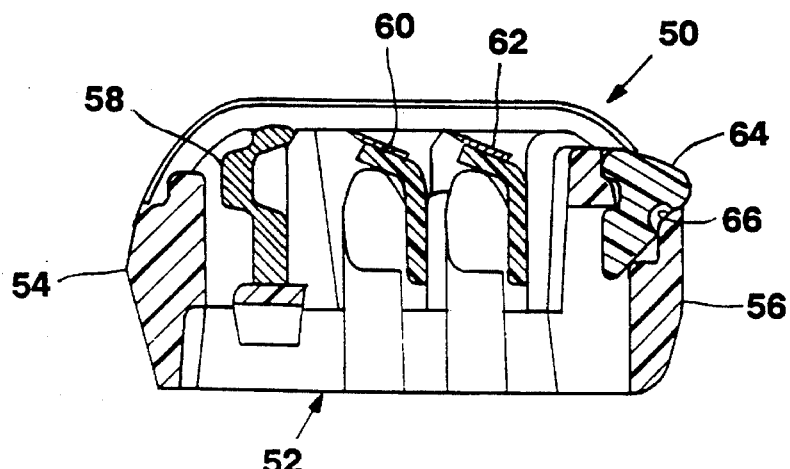
FIG. 3 is a perspective view of another razor unit in accordance with the invention.

The shaving unit 50 shown in FIG. 3 is of the type shown in Jacobson, U.S. Pat. No. 4,586,255, and includes body 52 with front portion 54 and rear portion 56. Resiliently secured in body 52 are guard member 58, leading blade unit 60 and trailing blade unit 62. A shaving aid composite in the form of elongated insert member 64 is frictionally locked in opening 66 of rear portion 56.

The shaving aid composite comprises a matrix of a water-insoluble polymer, an effective amount of a skin lubricating water-soluble polymer dispersed within the matrix, and a compatibilizer material that improves the compatibility of the water-soluble polymer with the water-insoluble polymer so as to reduce the domain size of the water-soluble polymer within the matrix and enhance release of the water-soluble polymer during use. The shaving aid composite may also optionally include low molecular weight water-soluble release enhancing agents such as polyethylene glycol, water-swellable release enhancing agents such as cross-linked polyacrylics, colorants, antioxidants, preservatives, microbiocidal agents, beard softeners, astringents, depilatories, medicinal agents, conditioning agents, cooling agents, etc.

Suitable water-insoluble polymers which can be used for the matrix include polyethylene, polypropylene, polystyrene, butadiene-styrene copolymer (e.g. medium and high impact polystyrene), polyacetal, acrylonitrile butadiene styrene copolymer, ethylene vinyl acetate copolymer and blends such as polypropylene/polystyrene blend. Preferably the water-insoluble polymer comprises about 10 to 50%, more preferably about 15 to 40%, and most preferably about 20 to 30% by weight of the shaving aid composite. The more preferred water-insoluble polymer is polystyrene, preferably a general purpose polstrene such as Dow STYRON (Dow Chemical Company) or a high impact polystyrene, such as Mobil 4324 (Mobil Corporation). The composite should contain a sufficient quantity of water-insoluble polymer to provide adequate mechanical strength, both during production and use.

Suitable skin lubricating water-soluble polymers include polyethylene oxide, polyvinyl pyrrolidone, polyacrylamide, hydroxypropyl cellulose, polyvinyl imidazoline, and polyhydroxyethylmethacrylate. Preferably the water-soluble polymer comprises about 20 to 90%, more preferably about 40 to 80%, and most preferably about 60 to 80% by weight of the shaving aid composite.

The more preferred water-soluble polymers are the polyethylene oxides generally known as POLYOX (available from Union Carbide Corporation) or ALKOX (available from Meisei Chemical Works, Kyoto, Japan). These polyethylene oxides will preferably have molecular weights of about 100,000 to 6 million, most preferably about 300,000 to 5 million. The most preferred polyethylene oxide comprises a blend of about 40 to 80% of polyethylene oxide having a molecular weight of about 5 million (e.g. POLYOX COAGULANT) and about 60 to 20% of polyethylene oxide having an average molecular weight of about 300,000 (e.g. POLYOX WSR-N-750).

The compatibilizer material may be any agent which has an affinity for both the water-insoluble polymer and the water-soluble polymer such that it improves the dispersibility of one polymer within the other and reduces the domain size of the water-soluble polymer within the matrix. It also changes the phase behavior and mechanical properties of the final polymer blend, making it softer while retaining structural integrity. Without being bound by any theory, it is believed that the compatibilizer material acts in polymer blends much in the same way as a surfactant does in oil and water systems.

In conventional shaving aid composites comprising primarily a dispersion of a polyethylene oxide lubricant in a polystyrene matrix, the domain size of the polyethylene oxide phase is typically in the range of about 30–100 μm when a cross-section of the composite is viewed by SEM. Shaving aid composites containing a compatibilizer material in accordance with the present invention generally have a water-soluble polymer domain size at least 50%, preferably at least 80%, smaller than that of similar composites without compatibilizer. Typically such composites will have a water-soluble polymer domain size under 10 μm, preferably about 1 μm or less.

Since the water-soluble polymer is dispersed more uniformly within the matrix due to the smaller domain size the new shaving aid composites have quite different mechanical properties (generally softer) compared to conventional composites and more readily release the water-soluble polymer from the matrix during shaving. In fact, the mechanical properties of the shaving aid composite can be adjusted by varying the levels of compatibilizer such that the entire composite (that is, both matrix and lubricant) gradually wears away during use, thus continuously exposing the user to a fresh composite surface providing excellent lubrication for numerous shaves. Generally the compatibilizer material will comprise about 0.5 to 15%, preferably about 1 to 10% and more preferably about 2 to 7% by weight of the shaving aid composite.

Suitable compatibilizer materials for use in accordance with the present invention include the following:

(a) Polyethylene oxide—polypropylene oxide copolymers, generally those having a molecular weight of about 1000 to about 20,000, preferably about 2000 to about 10,000, and an ethylene oxide: propylene oxide ratio of about 10:90 to about 80:20, preferably about 10:90 to about 50:50. These include, for example, Poloxamer 181 (CHEMAL BP-261), Poloxamer 182 (CHEMAL BP-262), Poloxamer 183 (PLURONIC L-63), Poloxamer 184 (PLURONIC L-64), Poloxamer 188 (PLURONIC F-68) Poloxamer 212 (PLURONIC L-72), Poloxamer 217 (PLURONIC F-77) Poloxamer 231 (PLURONIC L-81), Poloxamer 282 (PLURONIC L-92), Poloxamer 402 (PLURONIC L-122) and Poloxamer 403 (PLURONIC P-123).

(b) Polyethylene oxide-polypropylene oxide copolymers of ethylene diamine such as Poloxamine 702 (TETRONIC 702) Poloxamine 901 (TETRONIC 901) and Poloxamine 1101 (TETRONIC 1101).

(c) Polystyrene-polyethylene oxide copolymers.

(d) Alkyl polyglycol ethers such as Steareth-10 and Laureth-23.

(e) Fatty alkanolamides such as Lauramide MEA and Stearamide DEA.

(f) Alkyl polyethyleneimines such as lauryl polyethyleneimine.

(g) Anionic surfactants such as sodium lauryl sulfate and dodecylbenzene sulfonic acid.

(h) Cationic surfactants such as alkyl trimethyl ammonium salts, for example dodecyltrimethylammonium chloride.

The shaving aid composite may be formed by extrusion, injection molding or in situ molding on a razor cap. Extrusion is the preferred method and should normally be performed in a controlled environment to minimize moisture absorption during fabrication.

The invention may be further illustrated by the following example in which all parts and percentages are by weight.

EXAMPLE

Shaving aid composites similar to insert member 64 shown in FIG. 3 were fabricated from the blends indicated below by extruding the blends through a Haake System 90 ¾ inch diameter extruder with a barrel pressure of about 1000–1800 psi and a temperature of about 180°–185° C. and a die temperature of about 190° C. The extruded strip of composite is cooled and sliced to appropriate lengths for securing into openings 66 of shaving units 50. In all of the blends listed below, the polystyrene is Dow STYRON and the polyethylene oxide is a blend of 60% POLYOX COAGULANT (M.W. 5 million) and 40% POLYOX WSR-N-750 (M.W. 300,000).

Blend A

20% polystyrene
69% polyethylene oxide
10% polyethylene oxide-polypropylene oxide copolymer (CHEMAL BP-262)
1% white colorant Blend B 20% polystyrene
64% polyethylene oxide
3% crosslinked polyacrylic hydrogel (SALSORB 88)
5% polyethylene glycol (M.W. 4500)
7% polyethylene oxide—polypropylene oxide copolymer (CHEMAL BP-262)
1% white colorant Blend C 25% polystyrene 63% polyethylene oxide
3% crosslinked polyacrylic hydrogel (SALSORB 88)
3% polyethylene glycol (M.W. 4500)
5% polyethylene oxide—polypropylene oxide copolymer (CHEMAL BP-262)
1% white colorant Blend D 25% polystyrene
63% polyethylene oxide
3% crosslinked polyacrylic hydrogel (SALSORB 88)
3% polyethylene glycol (M.W. 4500)
5% dodecylbenzene sulfonic acid
1% white colorant Blend E 25% polystyrene
63% polyethylene oxide
3% crosslinked polyacrylic hydrogel (SALSORB 88)
3% polyethylene glycol (M.W. 4500)
5% polyethylene oxide—polypropylene oxide copolymer (PLURONIC F-77)
1% white colorant The shaving aid composites made from the above-identified blends provided greater release of polyethylene oxide over a longer period of time than conventional composites made without any compatibilizer. When subjected to a wool felt wear/leach test which simulates use, these shaving aid composites lost substantially more weight than similar strips without compatibilizer, while retaining good structural integrity.

What is claimed is:

1. A shaving system of the wet shave type comprising a blade member and structure defining an external skin engaging portion in proximity to said blade member, said skin engaging portion including a shaving aid composite comprising a matrix of a water-insoluble polymer, an effective amount of a skin lubricating water-soluble polymer dispersed in said matrix, and a compatibilizer material that improves the compatibility of the water-soluble polymer with the water-insoluble polymer so as to reduce the domain size of the water-soluble polymer within the matrix.

2. The shaving system of claim 1 wherein said water-soluble polymer comprises about 40% to about 80% by weight of said shaving aid composite and is selected from the group consisting of polyethylene oxide, polyvinyl pyrrolidone, polyacrylamide, hydroxypropyl cellulose, polyvinyl imidazoline, and polyhydroxyethylmethacrylate.

3. The shaving system of claim 2 wherein said water-insoluble polymer comprises about 15% to about 40% by weight of said shaving aid composite and is selected from the group consisting of polyethylene, polypropylene, polystyrene, polystyrene butadiene copolymer, polyacetal, acrylonitrile butadiene styrene copolymer, and ethylene vinyl acetate copolymer.

4. The shaving system of claim 3 wherein said water-insoluble polymer comprises polystyrene and said water-soluble polymer comprises polyethylene oxide.

5. The shaving system of claim 4 wherein said compatibilizer material comprises a polyethylene oxide-polypropylene oxide copolymer.

6. The shaving system of claim 5 wherein said polyethylene oxide-polypropylene oxide copolymer has a molecular weight of about 1000 to about 20,000 and an ethylene oxide: propylene oxide ratio of about 10:90 to about 80:20.

7. The shaving system of claim 6 wherein said water-soluble polymer comprises a blend of polyethylene oxide having an average molecular weight of about 5 million and a polyethylene oxide having an average molecular weight of about 300,000.

8. The shaving system of claim 7 wherein said compatibilizer material comprises about 0.5% to about 15% by weight of said shaving aid composite.

9. The shaving system of claim 3 wherein said compatibilizer material comprises about 0.5% to about 15% by weight of said shaving aid composite and is selected from the group consisting of polyethylene oxide-polypropylene oxide copolymers, polyethylene oxide-polypropyleneoxide copolymers of ethylene diamine, polystyrene-polyethylene oxide copolymers, alkyl polyglycol ethers, fatty alkanolamides, alkyl polyethyleneimines, anionic surfactants, and cationic surfactants.

10. The shaving system of claim 9 wherein said water-insoluble polymer comprises polystyrene and said water-soluble polymer comprises polyethylene oxide.

11. The shaving system of claim 1 wherein said shaving aid composite comprises about 20% to about 30% by weight polystyrene, about 60% to about 80% by weight polyethylene oxide and about 1% to about 10% by weight compatibilizer material.

12. The shaving system of claim 11 wherein said compatibilizer material is selected from the group consisting of polyethylene oxide-polypropylene oxide copolymers, polyethylene oxide-polypropyleneoxide copolymers of ethylene diamine, polystyrene-polyethylene oxide copolymers, alkyl polyglycol ethers, fatty alkanolamides, alkyl polyethyleneimines, anionic surfactants, and cationic surfactants.

13. The shaving system of claim 12 wherein the domain size of the polyethylene oxide within the matrix is less than 10 µM.

14. The shaving system of claim 11 wherein said compatibilizer material comprises polyethylene oxide-polypropylene oxide copolymer having a molecular weight of about 2000 to about 10,000 and an ethylene oxide: propylene oxide ratio of about 10:90 to about 50:50.

15. The shaving system of claim 11 wherein said compatibilizer material is Poloxamer 182.

16. The shaving system of claim 11 wherein said compatibilizer material is dodecylbenzene sulfonic acid.

17. The shaving system of claim 11 wherein said compatibilizer material is Poloxamer 217.

* * * * *

UNITED STATES PATENT AND TRADEMARK OFFICE
CERTIFICATE OF CORRECTION

PATENT NO. : 5,454,164
DATED : October 3, 1995
INVENTOR(S) : Yuling Yin et al.

It is certified that error appears in the above-indentified patent and that said Letters Patent is hereby corrected as shown below:

On the title page, add -- Lee K. Lim, Bethesda, Maryland -- as an inventor.

Signed and Sealed this

Twenty-eighth Day of May, 1996

Attest:

BRUCE LEHMAN

Attesting Officer     Commissioner of Patents and Trademarks